United States Patent [19]
Hadtke

[11] Patent Number: 5,449,379
[45] Date of Patent: Sep. 12, 1995

[54] APPARATUS FOR APPLYING A DESIRED TEMPERATURE AND PRESSURE TO AN INJURED AREA

[75] Inventor: Frederick B. Hadtke, New Providence, N.J.

[73] Assignee: Alternative Compression Technologies, Inc., E. Hampton, N.Y.

[21] Appl. No.: 95,436

[22] Filed: Jul. 21, 1993

[51] Int. Cl.⁶ ................................................ A61F 7/02
[52] U.S. Cl. ...................... 607/104; 607/112; 607/114; 606/203
[58] Field of Search .................. 607/96, 104, 108–112, 607/114; 606/201–203

[56] References Cited

U.S. PATENT DOCUMENTS

| | | |
|---|---|---|
| 3,186,404 | 6/1965 | Gardner ........................ 607/108 X |
| 3,643,665 | 2/1972 | Caillouette ........................ 607/114 |
| 3,683,902 | 8/1972 | Artemenko et al. . |
| 3,736,769 | 6/1973 | Petersen . |
| 3,776,241 | 12/1973 | Magilton et al. . |
| 3,780,537 | 12/1973 | Spencer . |
| 3,862,629 | 1/1975 | Rotta . |
| 3,871,381 | 3/1975 | Roslonski . |
| 3,882,867 | 5/1975 | Moran . |
| 3,885,403 | 5/1975 | Spencer . |
| 3,885,571 | 5/1975 | Sachs . |
| 3,901,225 | 8/1975 | Sconce . |
| 3,905,367 | 9/1975 | Dapcich . |
| 3,908,655 | 9/1975 | Lund . |
| 3,916,911 | 11/1975 | Sauder et al. . |
| 3,967,627 | 7/1976 | Brown . |
| 4,026,299 | 5/1977 | Sauder . |
| 4,044,773 | 8/1977 | Baldwin, III . |
| 4,055,188 | 10/1977 | Pelton . |
| 4,092,982 | 6/1978 | Salem . |
| 4,098,279 | 7/1978 | Golden . |
| 4,149,529 | 4/1979 | Copeland et al. . |
| 4,149,541 | 4/1979 | Gammons et al. . |
| 4,170,998 | 1/1980 | Sauder . |
| 4,184,537 | 1/1982 | Sauder . |
| 4,335,726 | 6/1982 | Kolstedt . |
| 4,338,944 | 7/1982 | Arkans . |
| 4,372,318 | 2/1983 | Viesturs et al. . |
| 4,396,010 | 8/1983 | Arkans . |
| 4,404,820 | 9/1983 | Romaine . |
| 4,414,969 | 11/1983 | Heyman . |
| 4,427,010 | 1/1984 | Marx . |
| 4,442,834 | 4/1984 | Tucker et al. . |
| 4,452,247 | 6/1984 | Hebert . |
| 4,459,468 | 7/1984 | Bailey . |
| 4,466,439 | 8/1984 | Moore . |
| 4,481,937 | 11/1984 | Arkans . |
| 4,556,065 | 12/1985 | Hoffmann . |
| 4,575,097 | 3/1986 | Brannigan et al. . |
| 4,592,358 | 6/1986 | Westplate . |
| 4,641,655 | 2/1987 | Abt . |
| 4,645,498 | 2/1987 | Kosak . |

(List continued on next page.)

Primary Examiner—Angela D. Sykes
Attorney, Agent, or Firm—Kenyon & Kenyon

[57] ABSTRACT

A portable apparatus for the treatment of injuries includes a first layer of flexible material and a second layer of flexible material coupled to the first layer of flexible material to form an inflation chamber. A third layer of flexible material is coupled to the first and second layers so that a space is formed between the second and third layers. The space formed between the second and third layers is in fluid communication with the inflation chamber at an outlet and the space between the second and third layers is formed so that a fluid channel extends from a first end of the space between the second and third layers to the outlet. A plurality of spacer members maintain the separation between the second and third layers so that the fluid channel remains unobstructed even when the apparatus is folded or wrapped around an injured area. The apparatus also includes an inlet to the fluid channel, the fluid channel being formed so that a gas entering the apparatus at the inlet will travel along the fluid channel through the outlet into the inflation chamber. The inlet may be coupled to a portable source of compressed gas and a relief valve is coupled to the inflation chamber so that the pressure within the inflation chamber is maintained at a predetermined pressure.

20 Claims, 6 Drawing Sheets

U.S. PATENT DOCUMENTS

| | | |
|---|---|---|
| 4,671,267 | 6/1987 | Stout . |
| 4,745,922 | 5/1988 | Taylor . |
| 4,753,241 | 6/1988 | Brannigan et al. . |
| 4,756,310 | 7/1988 | Bitterly . |
| 4,793,352 | 12/1988 | Eichenlaub . |
| 4,809,684 | 3/1989 | Gardner et al. . |
| 4,844,072 | 7/1989 | French et al. . |
| 4,846,176 | 7/1989 | Golden . |
| 4,869,250 | 9/1989 | Bitterly . |
| 4,898,148 | 2/1990 | Urso . |
| 4,910,978 | 3/1990 | Gordon et al. . |
| 4,913,957 | 4/1990 | Strack et al. . |
| 4,915,108 | 4/1990 | Sun . |
| 4,960,103 | 10/1990 | Urso . |
| 4,964,402 | 10/1990 | Grim et al. . |
| 5,065,758 | 11/1991 | Whitehead et al. . |
| 5,072,875 | 12/1991 | Zacoi . |
| 5,077,980 | 1/1992 | Weber . |
| 5,080,089 | 1/1992 | Mason et al. . |
| 5,088,478 | 2/1992 | Grim . |
| 5,097,829 | 3/1992 | Quisenberry . |
| 5,111,810 | 5/1992 | Fortney . |
| 5,117,812 | 6/1992 | McWhorter . |
| 5,123,411 | 6/1992 | Noziri . |
| 5,133,348 | 7/1992 | Mayn . |
| 5,169,384 | 12/1992 | Bosniak et al. . |
| 5,170,783 | 12/1992 | Smith . |
| 5,172,689 | 12/1992 | Wright . |
| 5,174,285 | 12/1992 | Fontenot . |
| 5,179,942 | 1/1993 | Drulias et al. . |
| 5,190,032 | 3/1993 | Zacoi . |
| 5,190,033 | 3/1993 | Johnson . |

APPARATUS FOR APPLYING A DESIRED TEMPERATURE AND PRESSURE TO AN INJURED AREA

FIELD OF THE INVENTION

The present invention relates to devices for applying heat and/or cold and pressure for the treatment of injuries.

BACKGROUND OF THE INVENTION

For the treatment of strains and sprains of joints, ligaments, tendons and muscles, the most commonly recommended treatment involves rest, ice, compression and elevation. A tenet of this treatment is that the sooner the treatment is started, the more effective it is.

Presently, cold treatment devices are available which utilize a variety of cooling and compression means including, for example, endothermic chemical packs and ice packs which may be held in place with elastic bandages and elaborate refrigerated water circulation systems.

Devices including ice packs and endothermic chemical packs have been frequently employed as they may be applied immediately. However, the ice is usually at a temperature of 28° F. or less, and may freeze the tissue causing frostbite. Also, the elastic bandages which are often used to secure these packs in place provide uneven compression and can cut off blood flow. In addition, as the ice melts, the pressure is reduced and the pack may slip out of position. Thus, this system requires close supervision to insure that the patient is properly and safely treated.

The equipment required for the refrigerated water circulation systems is so bulky that these systems are usually employed in a hospital or training room hours after the injury has occurred. This water circulation equipment is very expensive, complex and requires constant monitoring by the person providing care.

Ideally, doctors recommend that treatment be given for only 20 minutes at a time and that the pressure be limited to 0.4 psi over ambient and applied uniformly over a broad area, thereby preventing restriction of the blood circulation while adequately immobilizing the injured area. In addition, doctors recommend that cold be limited to no less than 36° F. for the 20 minute period and that both pressure and cold be uniformly applied during the treatment.

A prior device which provided portable, immediate cold and compression therapy is shown in U.S. Pat. No. 3,871,381. However, this device has several inherent drawbacks. This device is based upon three layers of material, two layers of which are heat sealed together so that a variety of tortuous pathways are formed. This assembly is then sealed to the third upper layer which extends around the perimeter of the wrap to form an inflatable cuff. A commutation between the end of the tortuous pathway and the inside of the outer layer exists to allow the expanded cooling agent to inflate the cuff. A valve on the upper surface may be adjusted to allow more or less gas to escape so that a desired compression of the wrap may be achieved. Velcro type attachment strips are used to secure the wrap around the injured limb.

However, when secured around the injured limb, the pressure in the inflated cuff closes off the tortuous pathway creating cold spots at various locations depending upon the contour of the limb being treated. When the valve is opened to reduce the pressure so that the tortuous pathway is unobstructed, the compression developed is insufficient to immobilize the area. The valves employed are comprised of numerous parts which, though inexpensive in their components, are expensive to assemble. They are also subject to intentional and inadvertent manipulation by the user so that, in practice, the pressure is often either above or below the doctors' recommended setting and varies during the treatment period. In addition, the device includes a plurality of baffles which extend into the tortuous pathway from the sealed sides in a direction counter to that of the flow through the pathway. These baffles trap small pockets of gas causing temperature variations over the surface of the device.

Finally, modifications to the design of compression wraps produced by the method shown in U.S. Pat. No. 3,871,381 are difficult and expensive to execute. These compression wraps are produced by sealing a variety of tortuous pathways and external configurations to achieve all-over cooling, localized cooling and specialized cooling of certain parts of the body. Each configuration requires a different sealing die which is very expensive to produce and mount onto the sealing equipment. Production of a variety of specialized wraps requires a large inventory of these expensive sealing dies.

Thus, there is a need for a device which provides portable, immediate cold and compression therapy and which provides a temperature and pressure which are uniform across the injured area and during the entire treatment period.

SUMMARY OF THE INVENTION

The present invention is directed to an apparatus for applying a desired temperature and pressure to an injured area which may be coupled to a portable source of compressed gas. The apparatus includes a first layer of flexible material and a second layer of flexible material coupled to the first layer of flexible material to form an inflation chamber. A third layer of flexible material is coupled to the first and second layers so that a space is formed between the second and third layers which is in fluid communication with the inflation chamber at an outlet. The space between the second and third layers defines a fluid channel which extends along a predetermined path from an inlet port to the outlet. The fluid channel is formed so that a gas entering the apparatus at the inlet will travel along the fluid channel through the outlet into the inflation chamber. In addition, a plurality of spacer members are provided between the second and third members. The spacer members, which are coupled to the second or third member, maintain the separation between the second and third layers so that the fluid channel remains unobstructed even when the apparatus is folded or wrapped around an injured area. A relief valve coupled to the inflation chamber maintains the pressure within the inflation chamber at a predetermined pressure.

DETAILED DESCRIPTION

Figure 1:
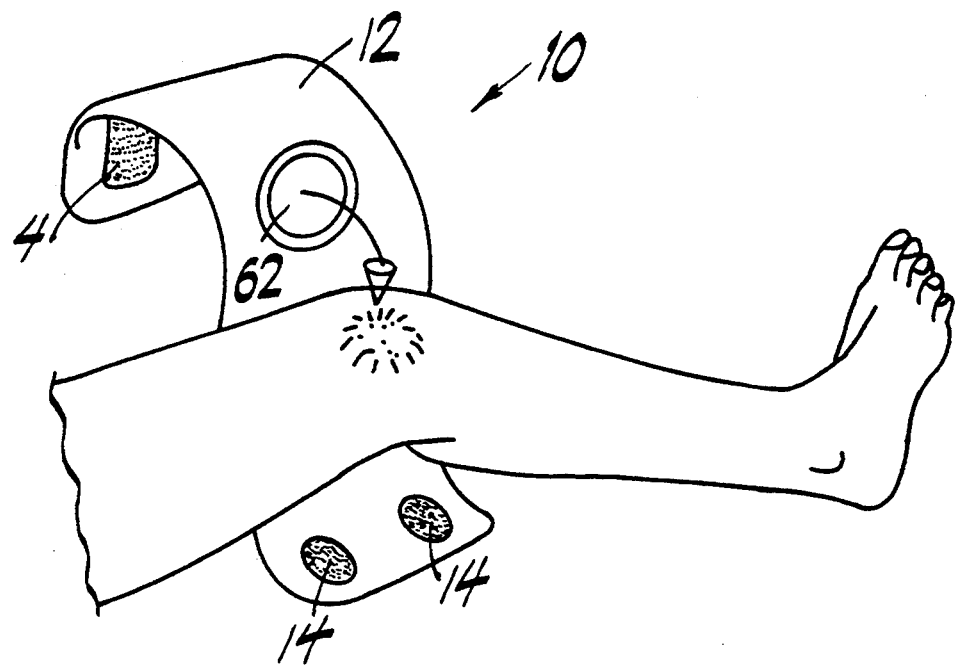
FIG. 1 shows an apparatus according to the present invention in a position prior to being placed around a patient's knee.
Figure 2:
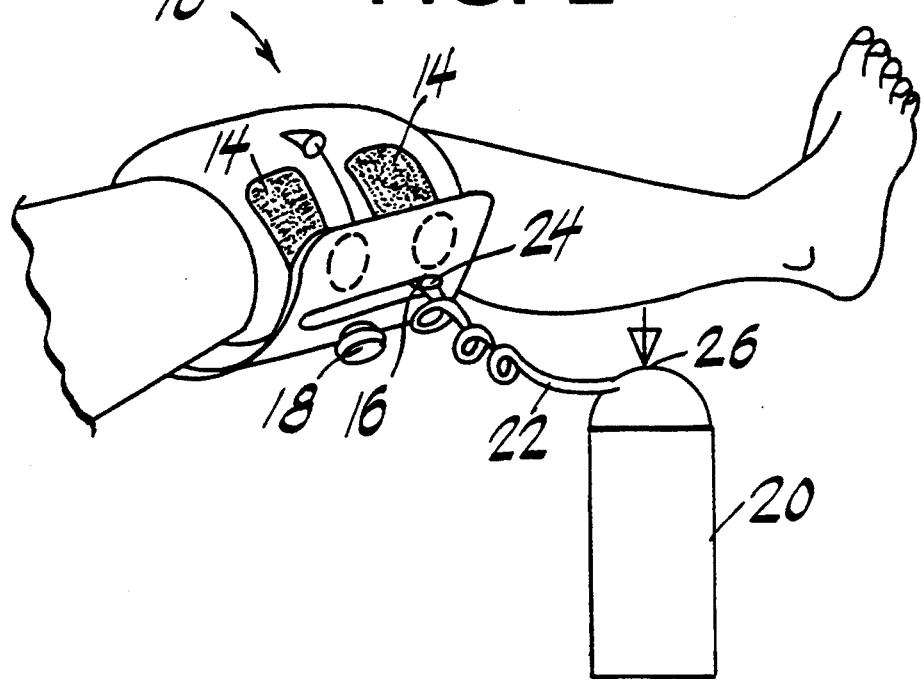
FIG. 2 shows an apparatus according to the present invention in position around a patient's knee and coupled to a source of compressed gas.
Figure 3:
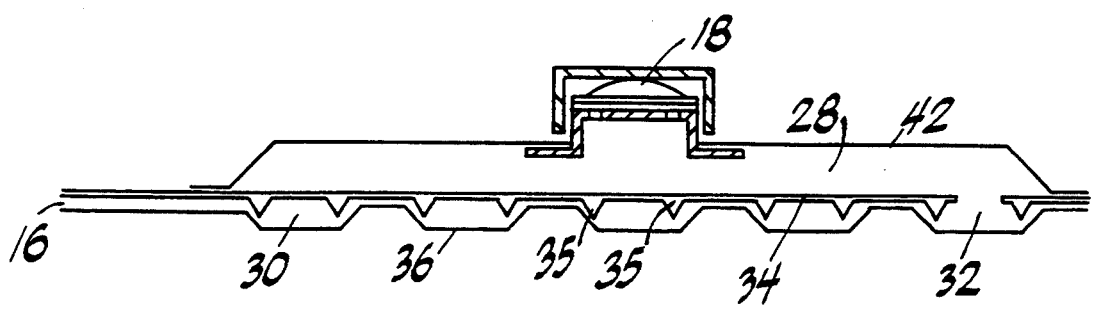
FIG. 3 shows a cross-section of an apparatus according to the present invention.

As shown in FIGS. 1–3, an apparatus according to the present invention is indicated generally by the numeral 10. The apparatus 10 includes a flexible wrap portion 12. The flexible wrap portion 12 may be held in place by means of adhesive strips or velcro attachments 14 which allow the wrap portion 12 to be firmly secured around an injured area of the body as shown in FIG. 2. Those skilled in the art will recognize that the apparatus 10 may be secured against or around any surface of the body by means of velcro fasteners, adhesive strips or other means known in the art. In addition, the apparatus 10 includes an inlet 16 and an outlet valve 18 which is mounted on an outer surface of the wrap portion 12. The apparatus may be coupled to a portable supply of a pressurized gas such as an aerosol can 20 by means of a flexible tube 22 one end 24 of which may be inserted into the inlet 16 while the other end 26 is coupled to the source of pressurized gas 20.

Figure 4A:
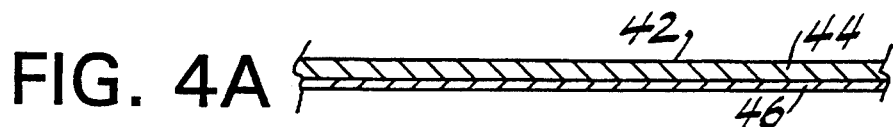
FIG. 4A shows a cross-section of a sheet of material used to form a top layer of an apparatus according to the present invention.
Figure 4B:
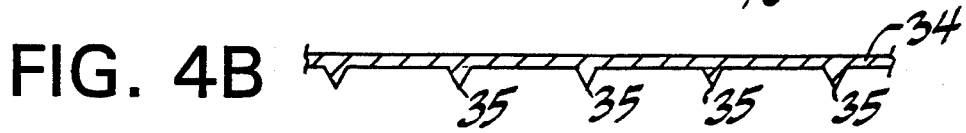
FIG. 4B shows a cross-section of a sheet of material used to form a spacer layer of an apparatus according to the present invention.
Figure 4C:
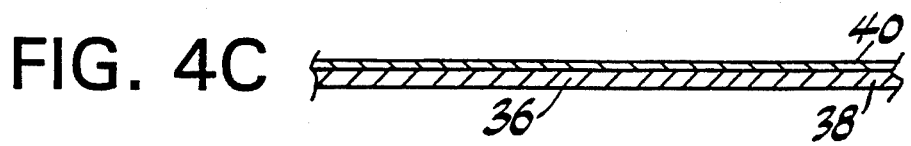
FIG. 4C shows a cross-section of a sheet of material used to form a bottom layer of an apparatus according to the present invention.
Figure 5:
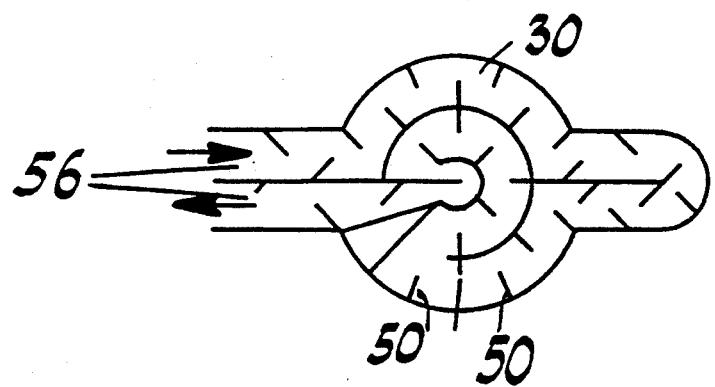
FIG. 5 shows a first pathway forming a fluid channel according to the present invention.
Figure 6:
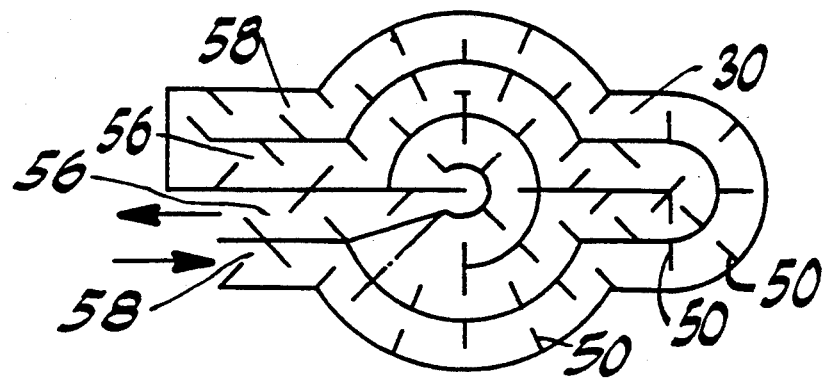
FIG. 6 shows a second pathway forming a fluid channel according to the present invention.
Figure 7:
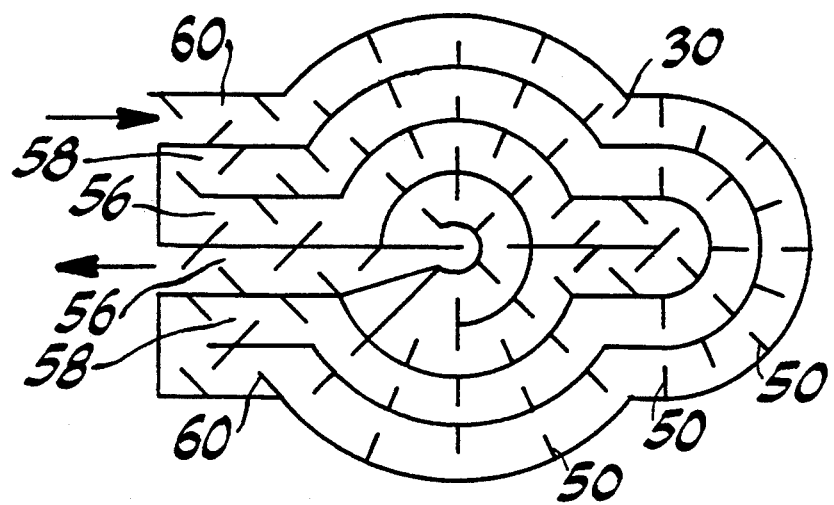
FIG. 7 shows a third pathway forming a fluid channel according to the present invention.
Figure 8:
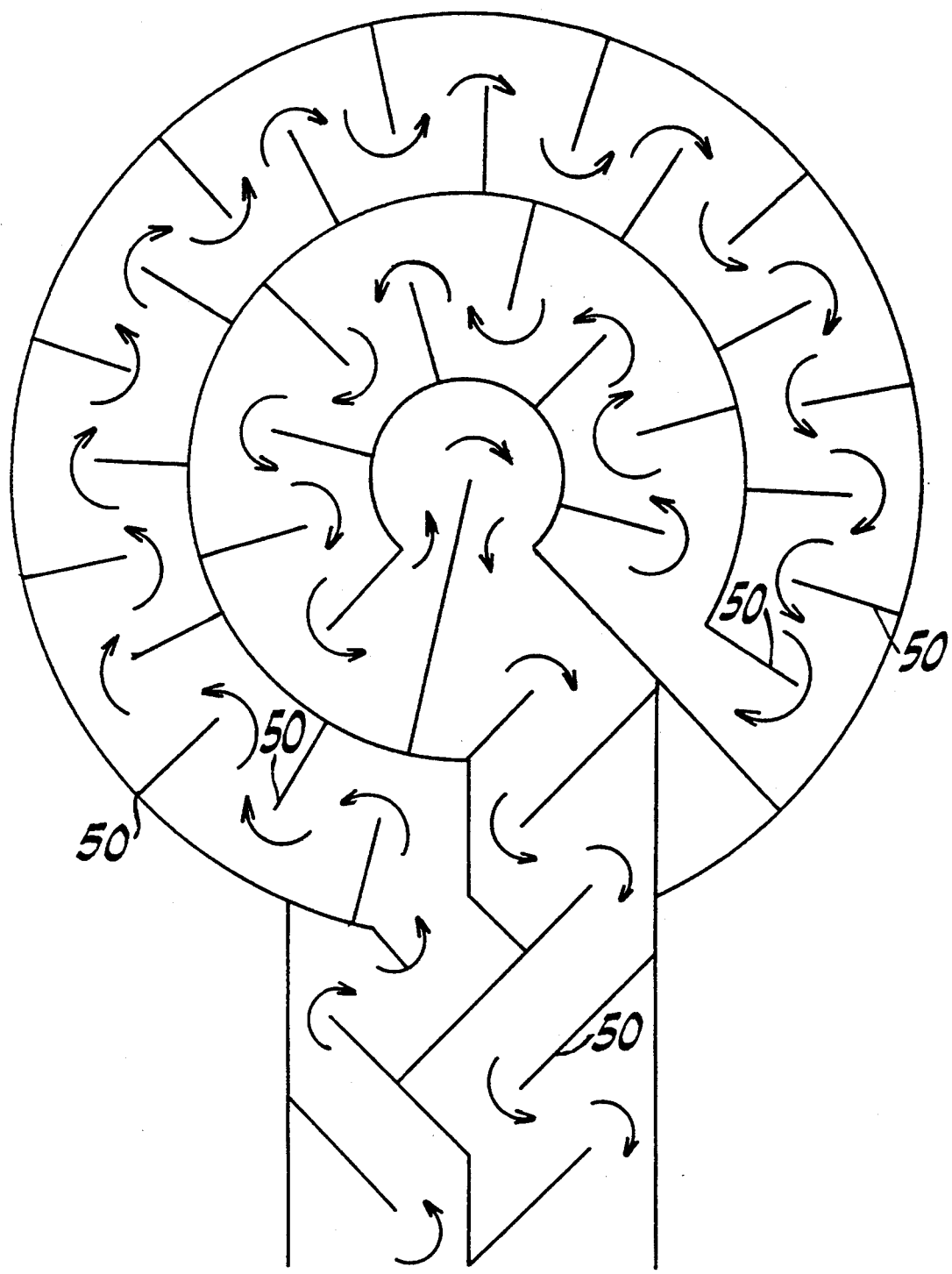
FIG. 8 shows a fourth pathway forming a fluid channel according to the present invention.
Figure 9:
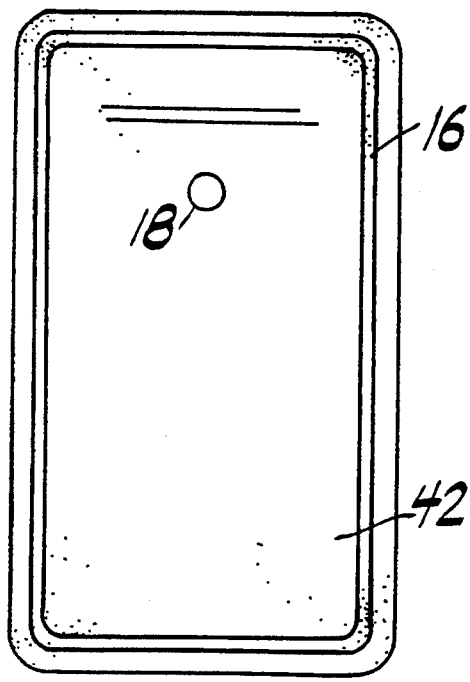
FIG. 9 shows a front view of an apparatus according to the present invention.

As shown in FIGS. 3, 4A–C and 9–11, the interior of the wrap portion 12 is made up of several layers of flexible material which form an inflation chamber 28, and a fluid channel 30 which leads from the inlet 16 along a tortuous or winding path to a port 32 which is in fluid communication with the inflation chamber 28. The fluid channel 30 is formed between a spacer layer 34 and a bottom layer 36. The spacer layer 34 is preferably formed of a flexible material such as PP or PVC while the bottom layer 36 is preferably formed of a sheet of woven nylon 38 with an interior coating 40 of PP or PVC, as shown in FIG. 4C. A top layer 42 of the wrap portion 12, is coupled to the spacer layer 34 and the bottom layer 36 so that the inflation chamber 28 is formed between the spacer layer 34 and the top layer 42. The top layer 42 is preferably formed of a woven nylon sheet 44 with a coating 46 of PP or PVC, as shown in FIG. A.

Figure 10:
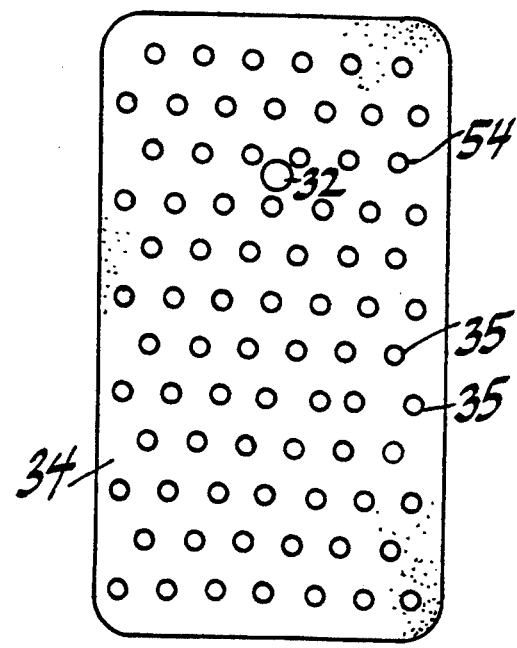
FIG. 10 shows a rear view of a spacer layer according to the present invention.

As shown in FIG. 4B, the spacer layer 34 may include integrally formed projections 35 which may extend from one or both sides of the layer 34. This spacer layer 34 may be formed from a dimpled sheet 54 of PP or PVC, as shown in FIG. 10.

In addition, a middle layer may optionally be disposed between the spacer layer 34 and the top layer 42. This allows the fluid channel 30 to extend over both sides of the spacer layer 34 before reaching the outlet 32. The middle layer may be formed of a nylon sheet with a coating of PP or PVC on both sides of the sheet. However, those skilled in the art will recognize that heat transfer will be more efficient when the fluid channel 30 is disposed on the side of the spacer layer 34 which faces the bottom layer 36. Therefore, if the fluid channel 30 is to extend across only one surface of the spacer layer 34, it is preferable to have the fluid channel 30 extend along this side of the spacer member 34.

As shown in FIGS. 5–8, the fluid channel 30 may be formed in a pattern as a series of independent pathways 56, 58 and 60 respectively, created by a multi-part tool. Thus, if a small localized wrap is needed, for example, for ankles, hands, wrists or necks, only the central portion of the tool is used to seal the pattern 56. If a medium sized wrap is needed, for example, for thighs, calves, biceps or shoulders an additional set of pathways, 56 in combination with 58, is created by using a sealing tool that fits around the central tool. Likewise, for a large wrap, for example, for treating the upper or lower back, a full leg or a full arm, a third pattern, added around the central tool, is installed to seal the outer pathway. Thus a pathway including 56, 58 and 60 is created. In this way, one tool with independently mounted sealing patterns may be employed to produce a variety of wraps which may be used to treat many areas of the body.

The patterns 56, 58 and 60 each contain a series of baffles 50 which extend into the fluid channel 30. The baffles 50 are oriented, relative to the directoin of flow in the fluid channel, so that no dead spots where stagnant pockets of gas would form, are created. These baffles increase the mixing and turbulence of the gas thereby ensuring uniform cooling.

Figure 11:
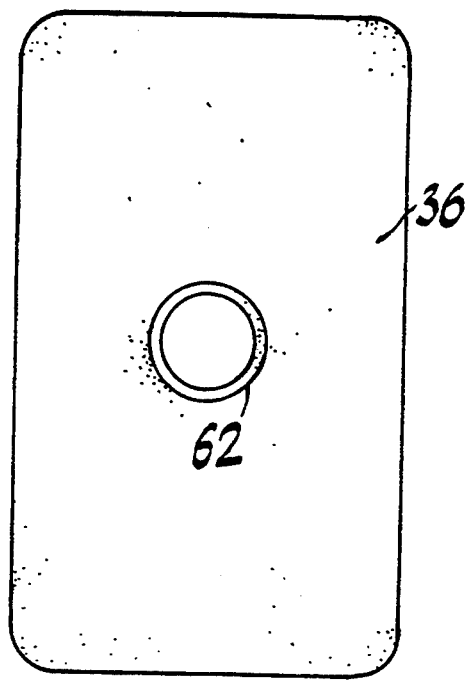
FIG. 11 shows an exterior view of an apparatus according to the present invention.

As shown in FIG. 11, the apparatus 10 may also include a target area 62 formed on the outer surface of the bottom layer 36. This target area 62 provides the user with a visual guide for the placement of the wrap portion 12 over the injured area. In addition, the target area 62 may be coated with a material which efficiently conducts heat. This material may be a mylar reinforced aluminum. Those skilled in the art will understand that the fluid channel 30 and the pathways 56, 58 and 60 are preferably arranged so that they are centered over the target area 62. This allows for more efficient heat transfer to or from the gas passing through the fluid channel 30.

Figure 13:
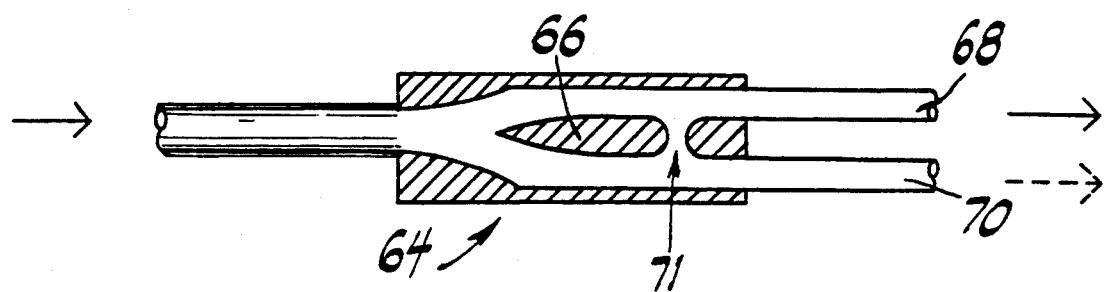
FIG. 13 shows a fluidic valve which automatically switches back and forth between alternate flow paths.
Figure 12:
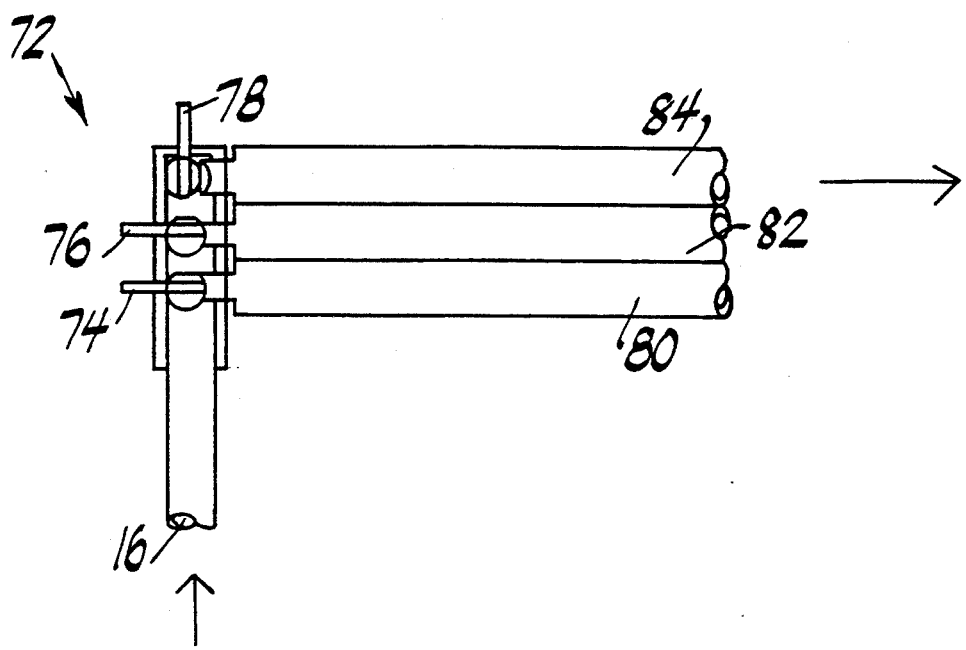
FIG. 12 shows a manifold for choosing one or more of a plurality of pathways for the flow of gas through an apparatus according to the present invention.

These independent tools also allow the pathways 56, 58 and 60, respectively, to be kept separate. Thus, separate areas around an injury may be treated individually. As shown in FIG. 12, the user could select a desired zone of treatment by means of a simple two or three position manifold 72 at the inlet 16. The manifold 72 allows the user to select one or more pathways which will receive gas from the inlet 16 by positioning the members 74, 76 and 78 to open or close the tubes 80, 82 and 84, respectively. In addition, a fluidic valve 64 as shown in FIG. 13, which includes an integrally molded member 66 will alternately divert the flow of a gas entering the inlet 16 to tube 68 and then to tube 70 due to the vacuum greated by the flow of the gas over the port 71. This allows the flow of gas to be switched back and forth from one pathway to another, to provide a soothing pulsation to the treatment. Alternatively, the pathways 56, 58 and 60, may be connected to form one extended pathway.

Those skilled in the art will recognize that an apparatus according to the present invention may be employed to provide compression and either heat or cold to an injured area and that the particular compressed gas employed in the apparatus will determine the temperature characteristics of the wrap. In addition, by varying the flow rate and the length of the tortuous path, various combinations of surface temperatures and pressures may be applied to the injured area. For cooling purposes $CO_2$, a halogenated hydrocarbon such as Dymel®, or any other known refrigerant gas may be employed. As known in the art, heat may be produced for application to the injured area through the use of a two phase mixture of gases to produce an exothermic reaction within the fluid channel 30.

As is known in the art, any of these compressed gases may be provided in a small canister equipped with a valve sized to accommodate the flexible tube 22. Thus, the apparatus according to the present invention is fully portable and may be applied immediately at the site of the injury.

There are many modifications of the disclosed apparatus which will be obvious to those skilled in the art. These modifications are considered to be within the scope of the invention which is to be limited only by the claims appended hereto.

What is claimed is:

1. A portable apparatus for the treatment of injuries which may be coupled to a portable source of compressed gas, the apparatus comprising:
    a first layer of flexible material;
    a second layer of flexible material coupled to the first layer of flexible material so that a space between the first and second layers forms an inflation chamber;
    a third layer of flexible material coupled to the first and second layers, said coupling between the second and third layers defining a space between the second and third layers, wherein the space between the second and third layers is in fluid communication with the inflation chamber at an outlet and wherein the space between the second and third layers defines a fluid channel which extends along a predetermined path from an inlet port to the outlet, wherein the fluid channel is formed so that a gas entering the apparatus at the inlet will travel along the fluid channel through the outlet into the inflation chamber;
    a plurality of spacer members coupled to one of the second and third layers, the spacer members maintaining the separation between the second and third layers so that the fluid channel remains unobstructed even when the apparatus is folded or wrapped around an injured area; and
    a relief valve coupled to the inflation chamber, wherein the relief valve operates to maintain the pressure within the inflation chamber below a predetermined pressure.

2. An apparatus according to claim 1 further comprising a plurality of baffles projecting into the fluid channel from at least one of the surfaces defining the fluid channel, wherein each baffle extends a distance into the fluid channel which is no more than ½ of the distance between the surface from which the baffle projects and a respective surface toward which it extends, and wherein the baffles are oriented so that dead spots where temperature discontinuities occur are not created.

3. An apparatus according to claim 1 wherein the spacer members are integrally formed with the second layer.

4. An apparatus according to claim 1 wherein the spacer members are integrally formed with the third layer.

5. An apparatus according to claim 1 wherein the third layer includes a target area formed of a material having a high thermal conductivity relative to the material which forms the rest of the third layer.

6. An apparatus according to claim 5 wherein the predetermined path is formed so that a ratio of the length of the fluid channel per unit area is greater in the target area than in the rest of the third layer.

7. An apparatus according to claim 5 wherein the target area is formed of mylar reinforced aluminum.

8. An apparatus according to claim 1 wherein the apparatus cools an injured area and applies compression to the injured area as gas from a portable source of compressed gas travels through the fluid channel.

9. An apparatus according to claim 1 further comprising means for coupling the apparatus to the body so that the third layer extends over at least a portion of the injured area.

10. An apparatus according to claim 9 wherein the means for coupling includes one of velcro attachments and adhesive strips.

11. An apparatus according to claim 1 further comprising at least one additional fluid channel which extends from the inlet to the outlet of the space between the second and third layers.

12. An apparatus according to claim 11 further comprising a valve which allows a user to select which of the fluid channels gas entering the inlet will travel through.

13. An apparatus according to claim 11 further comprising a valve which oscillates between a position wherein a first one of the fluid channels is in fluid communication with gas entering the inlet and a second position wherein a second one of the fluid channels is in fluid communication with gas entering the inlet.

14. (Amended) An apparatus according to claim 1 wherein the configuration of the relief valve is manually manipulable so that a user, by selecting a configuration of the relief valve, selects a desired maximum pressure within the inflation chamber.

15. An apparatus according to claim 1 wherein the spacer members are located within the space between the second and third layers so that the fluid channel is defined by the spacer members.

16. An apparatus for treating injuries, the apparatus being coupleable to a source of compressed gas at an inlet port, the apparatus comprising:
    a flexible, inflatable pouch which has a first sheet member including a first surface which, when in an operative position, is in contact with an injured area of the body and a second sheet member coupled to the first sheet member so that a fluid channel is formed between the first and second sheet members, the fluid channel being coupleable to the source of compressed gas at an inlet and extending along a predetermined path to an outlet which is in fluid communication with an inflation chamber formed between the first sheet member and the second sheet member so that gas travels from the inlet through the fluid channel along the predetermined path, through the outlet into the inflation chamber;

a plurality of spacer members disposed within the fluid channel, each spacer member being coupled to one of the first and second sheet members and resting slidably against the other of the first and second sheet members, wherein the spacer members resist compression of the fluid channel so that the fluid channel remains unobstructed even when the apparatus is folded or wrapped around an injured area; and a relief valve which maintains the pressure in the inflation chamber at a predetermined pressure.

17. An apparatus according to claim 16 wherein the spacer members are formed integrally with the second sheet member.

18. An apparatus according to claim 16 wherein the first surface is an outer surface of the first member.

19. An apparatus according to claim 18 wherein the first surface includes a target area, and wherein the target area includes a substance which has a higher thermal conductivity than does the material of the rest of the first surface.

20. An apparatus according to claim 16 wherein the relief valve is a molded silicon umbrella valve.

* * * * *